United States Patent

Seabrook et al.

[11] Patent Number: 5,554,373
[45] Date of Patent: Sep. 10, 1996

[54] COMPOSITIONS CONTAINING ANTI-MICROBIAL AGENTS AND METHODS FOR MAKING AND USING SAME

[76] Inventors: Samuel G. Seabrook; Richard C. Heymann, both of 1051 Planters Pl., Mount Pleasant, S.C. 29464

[21] Appl. No.: 149,211
[22] Filed: Nov. 5, 1993
[51] Int. Cl.[6] ........................................ A01N 25/34
[52] U.S. Cl. ........................ 424/400; 424/408; 424/404; 428/34.3; 428/35.2; 428/35.7
[58] Field of Search ........................... 424/404, 400, 424/408; 428/34.3, 35.2, 35.7

[56] References Cited

U.S. PATENT DOCUMENTS

| | | | |
|---|---|---|---|
| 3,864,468 | 2/1975 | Hyman et al. | 43/114 |
| 4,086,297 | 4/1978 | Rei et al. | 260/859 |
| 4,570,038 | 2/1986 | Tinelli | 179/185 |
| 4,624,679 | 11/1986 | McEntee | 8/650 |
| 4,661,528 | 4/1987 | Rei | 521/85 |
| 4,663,077 | 5/1987 | Rei et al. | 252/364 |
| 4,663,359 | 5/1987 | Rei | 521/85 |
| 4,666,706 | 5/1987 | Farquharson et al. | 424/408 |
| 4,666,956 | 5/1987 | Spielau et al. | 523/122 |
| 4,686,239 | 8/1987 | Rei | 521/55 |
| 4,747,902 | 5/1988 | Saitoh | 156/244.11 |
| 4,761,247 | 8/1988 | Rei et al. | 252/364 |
| 4,789,692 | 12/1988 | Rei et al. | 523/122 |
| 4,876,070 | 10/1989 | Tsukahara et al. | 422/122 |
| 4,888,175 | 12/1989 | Burton et al. | 424/409 |
| 4,891,391 | 1/1990 | McEntee | 523/122 |
| 5,063,706 | 11/1991 | Aki et al. | 43/125 |
| 5,229,124 | 7/1993 | Rei et al. | 424/409 |
| 5,354,210 | 10/1994 | Koblitz et al. | 439/276 |
| 5,360,350 | 11/1994 | Koblitz et al. | 439/276 |

FOREIGN PATENT DOCUMENTS

| | | |
|---|---|---|
| 0144726 | 6/1985 | European Pat. Off. . |
| 1169288 | 11/1969 | United Kingdom . |
| 90/11015 | 10/1990 | WIPO . |

OTHER PUBLICATIONS

Chemical Abstracts, Inoue, Mayumi, Study of Aseptic Packaging of Foods by Using 2-(4-thiazolyl)-benzimidazole in Plastic Film, vol. 89, 1978, p. 470.

Calgon Corporation, Metasol TK-100 Liquid Concentrate, Speciality Chemicals Group.

Primary Examiner—Thurman K. Page
Attorney, Agent, or Firm—Dority & Manning, P.A.

[57] ABSTRACT

Compositions containing anti-microbial agents and methods for making and using same are provided. Chemical controllers are added to the compositions for controlling the rate of release of the anti-microbial agents. The chemical controllers include vitamin E. A blend of anti-microbial agents can be included in the composition for destroying and inhibiting the growth of a wide variety of different microorganisms including bacteria, viruses, and fungi. Specifically, vitamin E has been found to control the rate of release of 10, 10'-oxybisphenoxarsine (OBPA) and 2 -(4'-thiazolyl) benzimadazole (TBZ). The anti-microbial agent(s) and the vitamin E are incorporated into polymeric materials. The polymeric materials can be formed into films, sheets, or tubing. Vitamin E controls the rate of migration of the anti-microbial agents so that harmful amounts of the anti-microbial agents are not released. The compositions have many applications, including uses in conjunction with agricultural products, food products, and consumables.

35 Claims, 3 Drawing Sheets

COMPOSITIONS CONTAINING ANTI-MICROBIAL AGENTS AND METHODS FOR MAKING AND USING SAME

FIELD OF THE INVENTION

This invention relates generally to compositions containing anti-microbial agents and more specifically to compositions for use in polymers wherein the rate of migration of anti-microbial agents from the polymers is controlled. Also included are methods of making the compositions containing the anti-microbial agents and methods of using the same.

BACKGROUND OF THE INVENTION

In recent years, polymers and plastics have become increasingly popular and important materials for making various types of articles. These articles, in turn, have been used in a limitless variety of applications. In some applications, the polymeric or plastic material, or an item contained in a polymeric or plastic article made therefrom is subject to attack and contamination by microorganisms. As such, a polymeric or plastic material capable of destroying or inhibiting foreign microorganisms would be desirable.

For instance, for the past three decades dentists have been warned that unusually high levels of microorganisms may be inhabiting dental unit water lines. Some of these microorganisms have been found to be pathogenic, meaning that they are capable of causing disease. This potential problem has recently been given great attention due to the increased number of immuno-compromised people caused in part by the spread of the HIV virus.

Dental unit water lines are particularly susceptible to invasion by microorganisms. These water lines are typically connected to a municipal water supply which contains very low levels of bacteria. However, when the water remains stagnant in the line, for instance overnight or over a weekend, bacteria will attach themselves to the polymer tubing and multiply. The resulting bacteria layer is known as a biofilm, a microbial mass attached to a surface that is bathed in liquids. Dental unit water lines have a very high surface area in proportion to the amount of water running through the lines which further promotes biofilm growth. Of course, biofilms can plague other polymeric articles, including household faucet lines, shower curtains, bathtub liners, garbage bags, surgical liners, tubing in air conditioners, or even artificial implants.

When present in dental unit water lines, the biofilms can separate from the tubing wall during operation causing bacteria to flow into a patient's mouth. Normally, a patient would not be susceptible to infection or disease unless the patient is immunity deficient. However, the potential always exists for infection.

In the past, solutions aimed at eliminating the biofilm problem have included flushing the line before each use. However, the water pressure in the line is typically not great enough to remove biofilms attached to the tubing walls. Further, because water flows in layers with the fastest moving layer being in the middle, the layer in contact with the tubing or the biofilm is stationary or slow moving. Although flushings will remove microorganisms loosely attached to the biofilm, it will not solve the greater biofilm problem.

Another proposed solution is to use water from an independent and sterile water source. However, such systems are expensive and also, through time, may become contaminated. Biofilms may develop if water lines are not flushed daily or the valves in the system maintained. Specifically, check valves would have to be installed into the system to ensure that used water is not retracted into the sterile water line.

Other suggestions to solve the biocide problem in dental tube lines have included the addition of filters or the use of chemical disinfectants. However, filters fail over time and cannot be easily monitored. Chemical disinfectants, on the other hand, may damage the equipment over time. Also, once biofilms are established, they are very resistant to disinfectants.

The present invention is concerned with solving the biofilm problem in dental tubing and overcoming the deficiencies of the above-suggested solutions. In general terms, the present invention relates to polymeric materials containing anti-microbial agents. The materials further include chemical controllers for controlling the rate of anti-microbial migration. In a particular application for dental tubing, anti-microbial agents and the chemical controllers are mixed with polymer compositions during formation of the tubing.

The anti-microbial agents contained within the tubing thereafter destroy the bacteria in the water flowing through the tube while the chemical controllers regulate the rate of release of the anti-microbial agents. The chemical controllers also ensure that the biocidal activity within the dental tube remains active for a substantial period of time and that large amounts of the anti-microbial agents are not released at once. Of course, dental tubing is only one specific application for the composition of the present invention.

The prior art discloses a number of examples of plastic materials containing biocidal materials but none have the particular characteristics of the present invention. For instance, U.S. Pat. No. 4,888,175 to Burtone et al., which is incorporated herein by reference in its entirety, discloses a plastic packaging material having a biocidal agent dissolved or dispersed therein. The biocidal agent used is 10,10-oxybisphenoxarsine which is an organically bound arsenic and will be referred to hereinafter as OBPA. The plastic material can be formed into a package for containing an organic material susceptible to bacterial or viral attack, such as plants, or the material may be formed in the shape of a dispensable liner for bathtubs.

U.S. Pat. No. 4,666,956 to Spielau et al. discloses a biocidal composition based on organic arsenic compounds. A tin compound is added to the composition to prevent elution of the arsenic compound. The compositions are used in the production of molded plastic articles, especially those vulnerable to biological attack.

U.S. Pat. Nos. 4,624,679 and 4,891,391, both to McEntee, disclose an anti-microbial and anti-oxidant composition preferably incorporated into a thermoplastic resin. The anti-microbial agents are incorporated into the thermoplastic materials during fabrication so that the resulting thermoplastic articles will resist microbial growth. The anti-oxidant is added so that the anti-microbial agent does not degrade during processing. OBPA is disclosed as one of the microbiocides.

An assortment of compositions containing microbiocides are disclosed in U.S. Pat. Nos. 4,686,239, 4,789,692, 4,086,297, and 4,663,077 in which Rei is listed as the inventor or one of the inventors. In the '239 patent, the '692 patent, and the '297 patent, a composition is disclosed wherein a microbiocide in high concentrations is added to a thermoplastic resin. The resulting concentrate is then incorporated into a second thermoplastic resin to produce a resulting article having the appropriate level of microbiocide. The second thermoplastic resin is added in an attempt to control the mobility of the microbiocide. One of the microbiocides disclosed is OBPA.

The '077 patent discloses a microbiocidal solution comprising an aryl alkanol solvent and a microbiocide compound dissolved therein. A plasticizer suitable for use as a polymer processing aid is added to the composition.

Sanitary covers for use on telephones and the like are disclosed in U.S. Pat. No. 4,570,038 to Tinelli. This sanitary cover includes an anti-microbial material for preventing transfer of bacteria or the like from the telephone to the user. The cover can be made from a plastic while the anti-microbial material may include OBPA.

Anti-bacterial materials and anti-microbial mixtures are disclosed in United Kingdom Patent No. 1,169,288 and European Patent Application No. 84113170.9. The United Kingdom patent is directed to a material having a base Sheet of plastic coated on one surface with a polymeric liquid composition containing an anti-bacterial agent capable of migrating through the sheet. The European patent application, on the other hand, discloses a mixture of a phenoxyarsine as an anti-microbial agent and a solvent. A plasticizer can be added to the mixture for incorporation into plastics.

Other prior art compositions containing biocides include U.S. Pat. No. 4,747,902 to Saitoh, U.S. Pat. No. 3,864,468 to Hyman et al., U.S. Pat. 4,666,706 to Farguharson et al., U.S. Pat. No. 5,063,706 to Aki et al., and U.S. Pat. No. 4,876,070 to Tsukahara et al.

Although the prior art shows a combination of biocidal compositions, the particular features of the present invention are absent from the prior art. Some of the prior art discloses materials containing small amounts of biocidal compositions for preventing bacterial attack on the material itself. However, most of the prior art does not show the use of biocidal materials in packaging films or sheets at a level such that the contents of the package, instead of the plastic itself, are inhibited against bacterial or viral growth. Further, the prior art is generally deficient in affording a composition that will not only control bacterial growth but that will also simultaneously control the growth of fungi. The prior art is also deficient in providing a polymeric composition containing anti-microbial agents wherein the rate of migration of the anti-microbial agents is controlled.

Although it is known to incorporate anti-microbial agents into plastics, the plastic products generally cannot be used for food and medical packaging applications unless extremely small amounts of biocide are used. However, small quantities of biocide will not protect the contents of the package adequately or protect the contents for an effective length of time from attack. Consequently, a need exists for a polymeric material containing anti-microbial agents wherein the rate of migration of the anti-microbial agents is controlled such that high dosages of the biocide are not released. Also, a need exists for a composition containing anti-microbial agents wherein the anti-microbial agent are released over an extended period of time. Further, a need exists for an anti-microbial composition that will inhibit the growth of bacteria and also fungi, viruses, and actinomycetes as well.

SUMMARY OF THE INVENTION

The present invention recognizes and addresses the foregoing disadvantages, and others of prior art constructions and methods.

Accordingly, it is an object of the present invention to provide an anti-microbial composition.

It is another object of the present invention to provide a polymeric composition containing anti-microbial agents.

It is another object of the present invention to provide a composition containing anti-microbial agents that will destroy bacteria and viruses as well as fungi.

It is another object of the present invention to provide a composition containing anti-microbial agents wherein the rate of release of the anti-microbial agents is controlled.

Another object of the present invention is to provide a multitude of polymer containing articles including a composition containing anti-microbial agents and chemical controllers for controlling the rate of release of the anti-microbial agents.

Still another object of the present invention is to provide a method of controlling the release of anti-microbial agents from a polymeric composition.

These and other objects of the present invention are achieved by providing an anti-microbial additive for adding to polymeric materials for destroying or inhibiting the growth of microorganisms. The anti-microbial additive includes a biocide including an organically bound arsenic and vitamin E. Vitamin is added in an effective amount for controlling the rate of release of the biocide when the biocide and the vitamin E are incorporated into a polymeric composition, such that the active concentration of the biocide within the polymeric composition is at a level capable of inhibiting the growth of microorganisms but is also at a level safe for human handling and for contact with consumables. As used hereinafter, the term active concentration refers to the concentration of the anti-microbial agents that are available for destroying and inhibiting the growth of microorganisms. The active concentration further refers to the anti-microbial agents that have been released from the materials that they are contained in. Also, the term consumables used hereinafter is defined as any food product, including, but not limited to, agricultural products. Consumables also refers to all drinkable liquids including water.

The organically bound arsenic in the anti-microbial additive can include 10,10'-oxybisphenoxarsine (OBPA). The OBPA can be added in a solid form or can be added contained in a liquid carrier. The liquid carrier can be epoxidized soybean oil. The OBPA can be added to polymeric materials in an amount from about 5 ppm to about 2,000 ppm and more preferably in an amount from about 50 ppm to about 500 ppm. The vitamin E can be added in an amount from about 50 ppm to about 2,000 ppm. The anti-microbial additive can further include 2-(4'-thiazolyl) benzimidazole (TBZ) which is a known fungicide.

The present invention is also directed to an anti-microbial additive for adding to polymeric materials for protecting such materials and other items in close proximity thereto from attack and infestation of microorganisms. The anti-microbial additive includes an organically bound arsenic for destroying and inhibiting bacteria, viruses, and other microorganisms. TBZ may also be included within the various components of the biocide for destroying and inhibiting fungi. Vitamin E in the formulation controls the rate of migration of the organically bound arsenic and the TBZ from a polymeric material such that the organically bound arsenic and the TBZ are released at active concentrations capable of inhibiting microorganisms while remaining at a level safe for human handling and for contact with consumables by the polymeric material. Again, the organically bound arsenic can include OBPA in the same amounts as listed above. The TBZ can be added in an amount from about 5 ppm to about 5,000 ppm.

The present invention also includes an aseptic material containing controlled release anti-microbial agents for inhibiting the growth of microorganisms. The composition includes an organically bound arsenic for destroying and inhibiting microorganisms and a polymeric composition in which the organically bound arsenic is dispersed. The composition further includes vitamin E for controlling the rate of release of the organically bound arsenic from the polymeric material at active concentrations for protecting the polymeric material and other items in close proximity thereto from attack and infestation of microorganisms. Further, the release of the organically bound arsenic is controlled at active concentrations safe for human contact and for contact with consumables.

The composition can further include TBZ for destroying and inhibiting the growth of fungi. The rate of release of the TBZ is also controlled by vitamin E. The polymeric material can include a polyalkalene, a polyolefin, a polyvinyl, a synthetic rubber, a latex fiber, a synthetic fiber, or mixtures thereof. The composition can be used to make films, sheets, tubings, and other plastic items.

Also included is an aseptic, polymeric material containing controlled release anti-microbial agents for inhibiting the growth of microorganisms. The composition includes an organically bound arsenic and TBZ for destroying and inhibiting bacteria, viruses, fungi, and other microorganisms. The composition includes a polymer in which the organically bound arsenic and the TBZ are dispersed. Vitamin E is added for controlling the rate of release of the organically bound arsenic and the TBZ from the polymeric material at active concentrations for inhibiting the growth of microorganisms and at concentrations safe for human contact and contact with consumables.

The organically bound arsenic can include OBPA in an amount from about 5 ppm to about 2,000 ppm. The TBZ can be added in an amount from about 5 ppm to about 5,000 ppm, while the vitamin E can be added in an amount from about 50 ppm to about 2,000 ppm. The vitamin E controls the rate of release of the anti-microbial agents such that the active concentration of arsenic within the composition is below about 50 ppb.

The present invention further includes an aseptic article containing controlled release anti-microbial agents for protecting the article and any contents therein from microbial infection or attack. The article includes a blend of anti-microbial agents including OBPA and TBZ for destroying and inhibiting the growth of a complete array of microorganisms including bacteria, fungi, and viruses. The article is typically made using a polymeric base material in which the anti-microbial agents are dispersed. Vitamin E is added for controlling the rate of migration of the anti-microbial agents from the article to any items in close proximity thereto.

Within the article, the OBPA can be present in an amount from about 5 ppm to about 2,000 ppm, the TBZ can be present in an amount from about 5 ppm to about 5,000 ppm, and the vitamin E can be present in an amount from about 50 ppm to about 2,000 ppm. Again, the vitamin E controls the rate of release of the anti-microbial agents such that the active concentration of arsenic in the article is below about 50 ppb.

The article can be used for a limitless variety of applications. For instance, the article can include dental tubing wherein the anti-microbial agents prevent the growth of biofilm within the tubing at active concentrations safe for human use. The article can also be in the form of agricultural granules for protecting agricultural products from attack by microorganisms or can take the shape of a plant container for protecting the plant from microbial attack. Also provided is an aseptic dental tubing containing controlled release anti-microbial agents for preventing the formation of biofilms therein. The dental tube comprises a blend of anti-microbial agents including OBPA and TBZ for destroying and inhibiting the growth of microorganisms found within the dental tube and within any water flowing therethrough. The dental tube can be made from a polymeric material in which the anti-microbial agents are dispersed. The tube can further include vitamin E for controlling the rate of release of the anti-microbial agents from the tube at active concentrations sufficient for destroying microorganisms but at levels safe for human use.

The polymeric material used to make the dental tubing can include polyvinylchloride, polyurethanes, nylons, polyethylenes, or mixtures thereof. Preferably, the OBPA is added to the tubing in an amount from about 50 ppm to 500 ppm, the TBZ is added in an amount from about 1,000 ppm to 3,000 ppm, and the vitamin E is added in an amount from about 500 ppm to about 1,500 ppm. The vitamin E can control the rate of release of the anti-microbial agents such that the active concentration of arsenic within the tube is below 50 ppb.

Also included is a method of controlling the release of anti-microbial agents from a polymeric composition. The method includes the steps of providing a polymeric material capable of being formed selectively into granules, films, sheets, and tubing. Anti-microbial agents include OBPA and TBZ. The method further includes adding vitamin E to the polymeric material for controlling the rate of release of the anti-microbial agents. The vitamin E can be added in an amount from about 50 ppm to about 2,000 ppm. The OBPA can be added in an amount from about 5 ppm to about 2,000 ppm, and the TBZ can be added in an amount from about 5 ppm to about 5,000 ppm. The polymeric material can include polyalkalenes, polyolefins, polyvinyls, synthetic rubbers, latex fibers, synthetic fibers, or mixtures thereof.

The compositions of the present invention can be used in an almost limitless variety of applications. Generally, the compositions are well suited for applications where it is desirous to prevent the growth of microorganisms upon the polymeric material itself or on and in products in close proximity to the material. For instance, the composition can be incorporated into a container or a film for protecting the contents thereof. The following is a list of possible applications. The list is not exhaustive but is merely provided for illustrative purposes.

FLORAL USES

Bucket liner

Bouquet sleeve

Bouquet wrap

Bunch sleeve

Corsage bag

Shredded plastic for box packing and shipping

Florafoam display blocks

Florafoam growing blocks

Potted plant sleeve

Shipping and display bag for bulbs

Shipping box liners

INDUSTRIAL USES

Inner liner for charcoal bags (high moisture barrier)

Inner liner for chemical containers and bags (high moisture barrier)

Inner liner for concrete bags (high moisture barrier)

Containers and tubing for industrial manufacturing

Shredded plastic for packing perishables

Stretch wrap for shipping and storage

AGRICULTURAL USES

Row crop plastic mulch (roll)

Shredded (Easter grass type) plastic for the packing of fruits and vegetables

Greenhouse frame covers

Greenhouse floor covering, table covering, etc.

Preformed container flats for plants

Granular mix for growing mediums (peat rock wool, etc.)

Drip irrigation tubing

Various plastic containers

Plastic sheeting for row crop forcing tunnels

MEDICAL AND DENTAL USES

Dental tubing and other medical tubing

Active anti-microbial barriers

Bio-Liners (trays, containers, etc.)

Contaminated waste disposal bags ("Red Bags")

Disposable devices packaging

Dust covers

Equipment covers (operatories)

Gloves

Glove liners

Hamper liners (soiled linens and diapers)

Isolation gowns, caps and show covers

Laundry bags for sterile/clean linens

Mattress covers and incontinent liners

Non-woven polymer air filtration elements

Orthopaedic appliance packaging

Surgical drapes

Surgical liners

MISCELLANEOUS PRODUCTS

Animal litter additive (granular)

Animal litter container liners

Veterinary products

Hygiene disposal bags

Other objects, features, and aspects of the present invention are discussed in greater detail below.

BRIEF DESCRIPTION OF THE DRAWINGS

A full enabling disclosure of the present invention including the best mode thereof to one of ordinary skill in the art, is set forth more particularly in the remainder of the specification, including reference to the accompanying figures in which.

Figure 1:
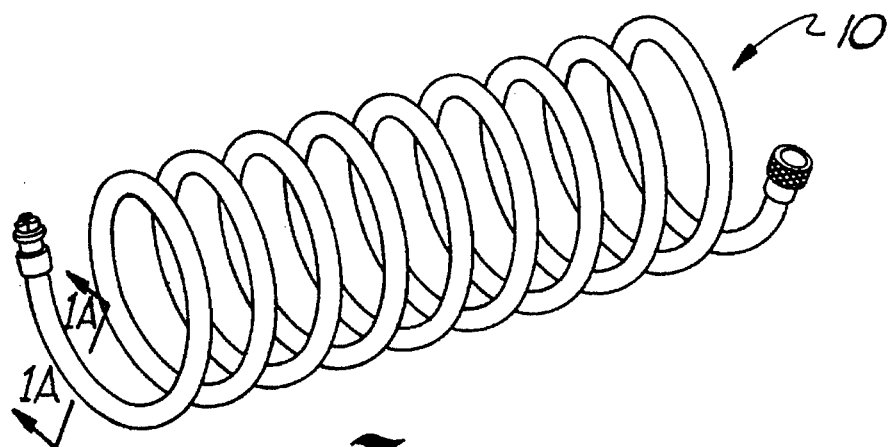
FIG. 1 is a perspective view of a piece of dental tubing made from the composition of the present invention.

Repeat use of reference characters in the present specification and drawings is intended to represent same or analogous features or elements of the invention.

DETAILED DESCRIPTION OF PREFERRED EMBODIMENTS

In general terms, the present invention is directed to a composition containing anti-microbial biocides and methods of making and using the same. The rate of migration or, in other words, the rate of release of the anti-microbial agents out of the composition is controlled by using a chemical controller. The chemical controller regulates the release of the anti-microbial agents so that the composition retains its microbiocidal characteristics for an extended period of time. One of the important advantages of the present invention is that the composition can be made into plastic articles to protect food products, house plants, and act as water lines. The chemical controller can be added in sufficient quantities to ensure that the active concentration of the anti-microbial agents is at levels that are safe for human contact.

The composition of the present invention is directed to a base polymeric material containing biocides. Preferably, these anti-microbial agents are dispersed within the polymeric base composition. Vitamin E is added to control the rate of release of the anti-microbial agents from the polymer material formed from the polymer composition.

Vitamin E is made from a mixture of tocopherols. As used here, vitamin E is defined as a substance containing a singular tocopherol or any mixtures thereof.

Vitamin E may control a variety of anti-microbial agents. One particular class of compounds whose rate of release controlled by vitamin E according to the present invention are the phenoxarsines. Phenoxarsines are organically bound arsenic compounds which are considerably less toxic than pure arsenic. However, since even small amounts of arsenic are considered to pose health threats, organically bound arsenic, by itself, has not previously been used in compositions to protect consumables.

A readily available organically bound arsenic is OBPA (10,10'-oxybisphenoxyarsine) which is marketed under the trade name VINYZENE. VINYZENE is sold at 1 percent or 2 percent concentrations in various plasticizers, for example, epoxidized soybean oil and in various phthalate esters. VINYZENE is also sold at a 5 percent concentration as a pelletized solid polymeric resin. Any particular form can be used in the present invention and can be effectively controlled by vitamin E.

OBPA is an effective anti-microbial agent for inhibiting the growth of a plurality of microorganisms. Particularly, OBPA is an effective biocide against bacteria and viruses. OBPA is a preferred anti-microbial agent because of its wide scope of inhibition and because of its ability to specifically inhibit different pathogens.

Another class of compounds found to be controlled by vitamin E are the benzimidazoles. Benzimidazoles are known as effective fungicides. One particular benzimidazole is 2-(4'-thiazolyl)benzimidazole which is also known as TBZ. TBZ is not nearly as toxic as the organically bound arsenics.

In a preferred composition of the present invention, vitamin E is used to control the rate of release of OBPA and TBZ combined in the same material. The resulting composition will exhibit biocidal activity against a wide array of microorganisms. The composition will destroy or inhibit the growth of bacteria, viruses, and fungi. This is particularly important because, in many applications, the object that is to be protected from microbial infestation is subject to attack from more than one variety and species of microorganism. The following table is illustrative of some of the microorganisms that may be inhibited by the present invention.

Fungi
*Alternaria tenuis*
*Alternaria Brassiciola*
*Aspergillus clayatus*
*Alternaria porri*
*A. longipes*
*Ascochyta pisi*
*Aspergillus flavus*
*Aureobasidium (Pullularia) pullulans*
*A. flavus*
*A. fumigalus*
*A. niger*
*A. ochracepus*
*A. oryzae*
*A. phocnicis*
*A. tamari*
*A. Terraus*
*A. ustes*
*A. wenlii*
*A. Versicolor*
*Botryodiplodia theobromae*
*Botrytis cinerea*
*B. gladiolorum*
*B. tullpae*
*Botryosphaeria spp.*
*Candida guilliermondii*
*Ceratocystis fimbriala*
*C. lipolytica*
*C. tropicalis*
*C. paradoxa*
*C. ulmi*
*Cercospora apli*
*C. asparagi*
*C. beticola*
*C. kikuchii*
*C. musae*
*C. nicotianau*
*C. oryzae*
*C. personata*
*C. solina*
*Cercosporealla spp.*
*Chaeeomium globosum*
*Cladosportum spp.*
*Cladosporium resinae*
*Clavicaps purpurea*
*Colletotrichum lindemuthianum*
*C. trifolii*
*C. truncatum*
*Certicium solani*
*Cylindrocladium spp.*
*Dactylium dendroldes*
*Deightoniella torulosa*
*Deuterophomia trachniphila*
*Diaporthe spp.*
*Diaporthe phaseolorum var. sojae*
*Diplodia spp.*
*Endothia parasitica*
*Erysiphe cichoracearum*
*F. graminis*
*Epicoccum nigrum*
*Fusarium culmorum*
*Fusarium moniliforme*
*F. gladioli*
*F. graminearum*
*F. nivale*
*F. moniliforme*
*F. oxysporum*
*F. roseum*
*F. solani*
*Fusiciadium effusum*
*Gibberella fujikuroi*
*Gliocladium virens (Trichoderms sp.)*
*G. zeae*
*Gloeosporium album*
*G. perennans*
*G. ribis*
*Glomerella cingulata*
*Helminthosporium gramineum*
*Helminthosporium solani*
*Lonzites trabea*
*Melanconlum elaeidis*
*Memnoniella echinata*
*Monilinia fructicola*
*M. Laxa*
*Monilochaetes infuscans*
*Mycogone perniciosa*
*Mycosphaerelia arachidicola*
*M. musicola*
*Mucor racemosus*
*Myrothecium verrucaria*
*Nigrospora musae*
*N. sphaerica*
*Oidium spp.*
*Oospora pusiulans*
*Ophiobolus spp.*
*P. cyclopium*
*P. digitatum*
*P. expansum*
*P. italicum*
*Pestalotia spp.*
*Penicillium citrinum*
*Penicillium islandicum*
*Phoma exigua*
*P. expansum*
*P. funiculosum*

*P. lilacinum*
*P. luteum*
*P. piscarium*
*P. variabile*
*P. foveata*
*P. terrostris*
*Phomopsis spp.*
*Phytlostictina musarum*
*Phymatotrichum omnivorum*
*Pithomyces chariarum*
*Plenodomus destruens*
*Podosphaera leucotricha*
*Pseudopeziza ribis*
*Pullularia pullulans*
*Pyricularia grisea*
*P. oryzae*
*Rhizopus higricans*
*Rhizoctonia solani*
*Sclerotinia homoeocarpa*
*S. sclerotiorum*
*Sclerotium bataticola*
*S. cepivorum*
*S. rollsii*
*Scopulariopsis spp.*
*Septoria apii*
*S. glycines*
*S. nodorum*
*S. tritici*
*Sphaerothaca macularis*
*Spicaria violacea*
*S. mors-uvae*
*S. pannosa*
*Stachybotrys spp.*
*Thanatephorus cucumeris*
*Thielaviopsis basicola*
*T. paradoxa*
*Trichophyton mentagrophytes*
*Trichoderma viride*
*Tilletia carles*
*T. contraversa*
*T. foetida*
*Trichothecium roseum*
*Urocystis agropyri*
*Ustilago strliformis*
*U. zeae*
*Vanturla inaequalis*
*V. pirina*
*Verticillium albo-airum*
*V. dahliae*
*V. theobromae*
Bacteria
*Aerobacter aerongenes*
*Bacillus cerous*
*Bacillus aubtilis*
*Desulfovibrio desulfurica*
*Escherichia coli*
*Klebsiella pneumoniae*
*Pseudomonas aeruginosa*
*Salmonella choleraesuis*
*S. typhimurlum*
*S. typhosa*
*Staphiococcus aureus*
Actinomycetes
*Stretomyces reubrireticuli*
*Streptoverticillium reticulum*
*Thermoactinomyces vulgaris*

Vitamin E and anti-microbial agents are preferably incorporated into a polymeric material. A polymeric material is preferably chosen that can be formed into films, sheets, and tubing besides having the ability to be formed into other articles. The anti-microbial agents and the vitamin E as discussed herein have been found to be compatible with a wide variety of polymers, plastics, and other materials. Preferably, the chemical controller and the anti-microbial agents are placed into a hydrocarbon based material. Examples of such polymeric materials include polyalkalenes, polyolefins, polyvinyls, synthetic rubber, latex fiber, synthetic fiber, and mixtures thereof. Other useful polymers include polyethylenes, polypropylenes, polystyrenes, polyacrylates, polyvinylchlorides, polyurethanes, and mixtures thereof. The base material can further include homopolymers or copolymers. The particular polymer used depends mostly upon the application. For instance, nylons, polyvinylchlorides, and polyurethanes are preferably used in dental tubing applications because of their flexibility and physical characteristics.

The amounts of the anti-microbial agents and the chemical controllers added to the composition are also dependent upon the particular application. Factors to consider are the conditions under which the composition is to be used, the microorganisms to be inhibited, the duration of the use, whether the object to be protected is a consumable, and the active concentration of the anti-microbial agents that is desired. The amount of OBPA to be added is limited in large part by its toxicity. The OBPA can be added in an amount from about 5 ppm to about 2,000 ppm. Preferably, the OBPA is present in an amount from about 50 ppm to about 500 ppm.

The TBZ, because it is not as toxic as the OBPA, is limited in the amount added mostly because of economics, TBZ being relatively expensive. Generally,, TBZ is added in an amount from about 5 ppm to about 5,000 ppm. Preferably, the TBZ is added in an amount from about 500 ppm to about 3,000 ppm.

The amount of vitamin E added to the composition is basically dependent upon the amount of control necessary over the anti-microbial agents. Thus far, vitamin E has been added in amounts from about 50 ppm to about 2,000 ppm. Preferably, vitamin E is added in an amount of about 1,000 ppm. These amounts generally correspond to aggressive regulation and control of the arsenic in the phenoxarsines. Based on recent United States Food and Drug Administration (FDA) restrictions and standards, the active concentration of arsenic is preferably limited to around 50 ppb. Also, the active concentration of TBZ is preferably limited to around 10 ppm. These limits are particularly important when the composition of the present invention is used in conjunction with consumables and other agricultural products. It has been found that approximately 1,000 ppm of vitamin E will effectively control the rate of release of OBPA and TBZ when present in the amounts specified above.

When making the compositions of the present invention, the hydrocarbon base material is preferably first heated. The anti-microbial agents and the vitamin E are then added either together or one at a time (if more than one agent is employed in the biocide). The mixture is then mixed until the anti-microbial agents and the chemical controllers are evenly dispersed within the polymeric composition. Other additives, such as plasticizers and dyes, can be added without affecting the anti-microbial agents or the chemical controllers. In fact, some plasticizers or other ingredients may be added to enhance the resulting physical characteristics of the composition. Accelerators such as ethylene methyl acrylate (EMA) may also be added. Such accelerators may reverse or limit the effects of the chemical controllers.

The resulting composition can be extruded, blown, or molded into various articles as listed above. The following is a list of products that may incorporate the composition of the present invention.

Figure 1A:
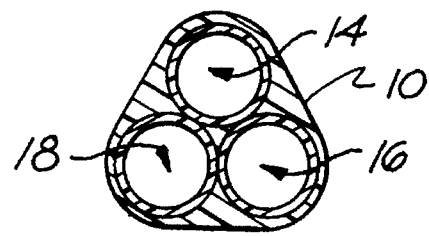
FIG. 1A is a sectional view of the dental tubing of FIG. 1 taken along line 1A—1A.

One particular product incorporating the composition of the present invention as illustrated in FIG. 1 is dental tubing shown generally as 10. Dental tubing is typically multi-channeled having up to five different channels within an outer coating. Dental tubing 10 in FIG. 1 has three channels 14, 16, and 18. Dental tubing 10 is connected to a hand piece (not shown) containing a drill and other instruments for use by a dentist. Tubing 10 supplies water and air to the hand piece. As shown in FIG. 1A tubing 10 includes a water channel 14, an air channel 16, and a water/waste return 18. As discussed above, water channel 14 is susceptible to biofilm development. The composition of the present invention can be used in the manufacture of tubing 10. The composition can be incorporated into channel 14 or can be incorporated into the entire tubing 10. Preferably, the composition incorporated into tubing 10 includes vitamin E, TBZ, and OBPA. Most preferably, the amount of vitamin E added is approximately 1,000 ppm, the amount of TBZ added is approximately 2,000 ppm, and the amount of OBPA added is approximately 400 ppm.

Figure 2:
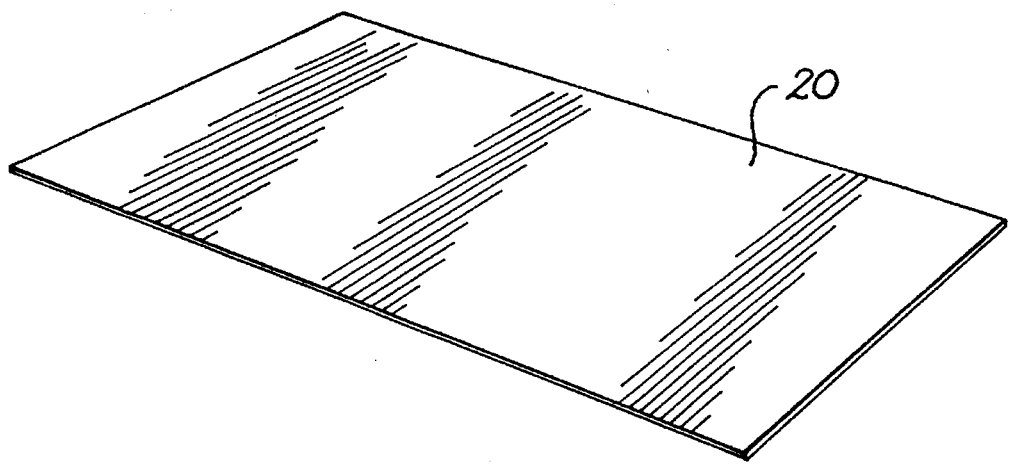
FIG. 2 is a plan view of a sheet prepared in accordance with the present invention.

Besides tubing, the composition of the present invention can also be made into a sheet 20 as shown in FIG. 2. Sheet 20 can then be formed into various packages and articles. For instance, sheet 20 can be used to make cat litter boxes. In one embodiment, a cat litter box contains OBPA in an amount of approximately of 500 ppm, TBZ in an amount of approximately 1,000 ppm and vitamin E in an amount of approximately 1,000 ppm.

Figure 3:
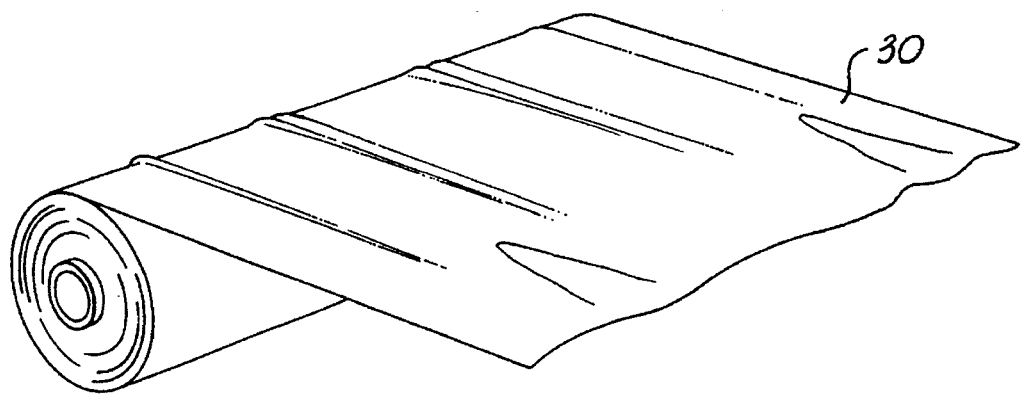
FIG. 3 is a perspective view of a roll of polymeric film made in accordance with the present invention.

Referring to FIG. 3, the composition of the present invention can also be incorporated into a film 30. Film 30 can be used for a variety of liners and wraps. One of the biggest problems faced by shipper and exporters of fresh produce is the relatively short life of fresh fruits and vegetables. Many produce items are shipped great distances, requiring a significant amount of travel time. Film 30 can be used to wrap fruits and vegetables for increasing their shelf life by protection then from microbial infestation.

Figure 4:
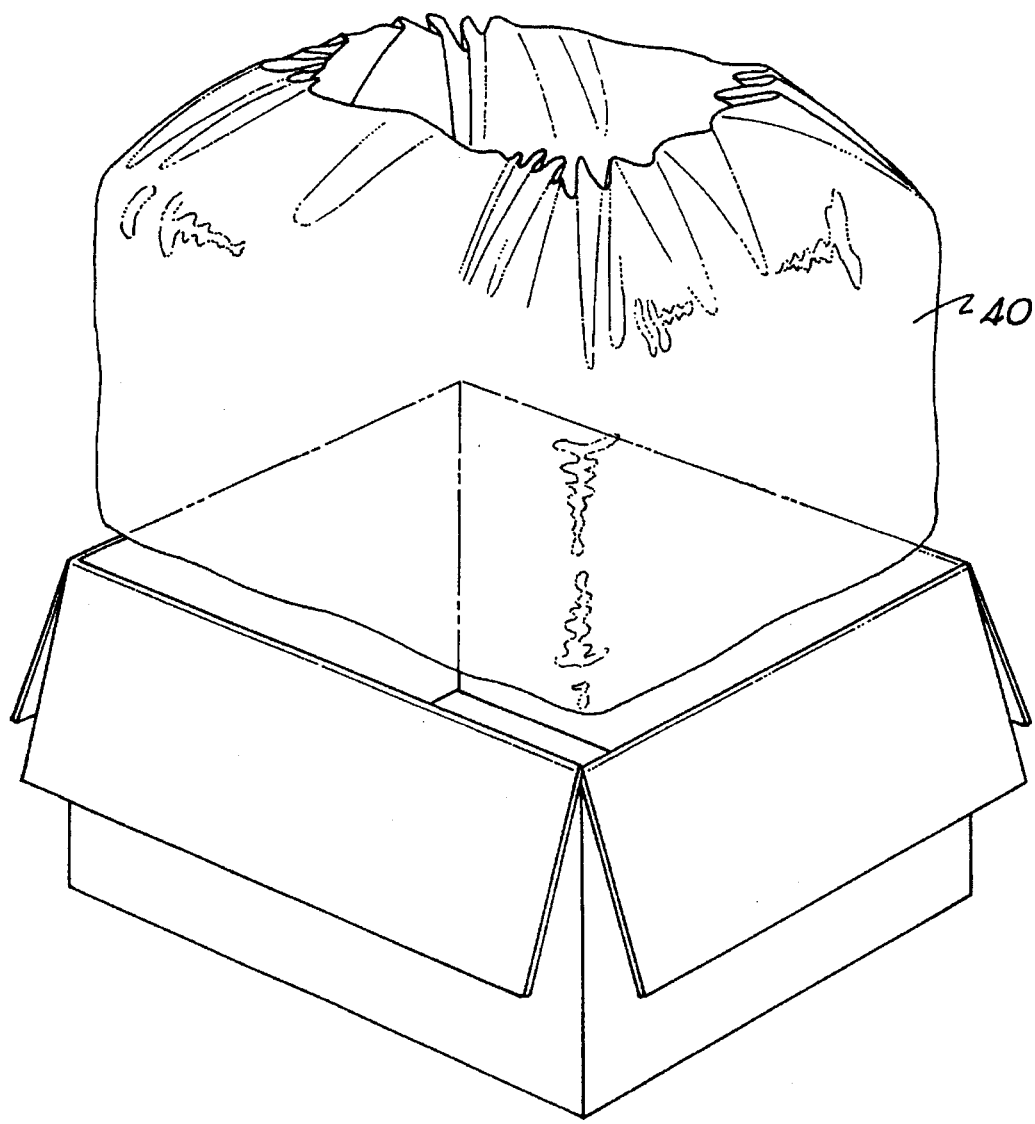
FIG. 4 is a perspective view of a box liner made in accordance with the present invention.

Referring to FIG. 4, a liner 40 is shown made from film 30 in FIG. 3. Liner 40 also may be used for a number of applications. For instance, liner 40 can be used for the transportation and shipment of cut flowers. As with produce, cut flowers typically have a short shelf life and are prone to attack by microorganisms. Liner 40 could be used to cover and protect any such plants.

Other uses for liner 40 include holding infectious wastes. With a recent epidemic of the HIV virus, infectious wastes generated by hospitals, clinics, and laboratories has created disposal concerns. Liner 40 could be used to contain such wastes and control pathogens which may leak or spill onto the outer surface of the bag and infect handlers. Liner 40 may also be used for a cat litter box liner. Preferably, the product contains 500 ppm OBPA, 1,000 ppm TBZ, and 1,000 ppm vitamin E for the control of any microorganisms found within the cat litter. The product could be used without threat to any pets.

Figure 5:
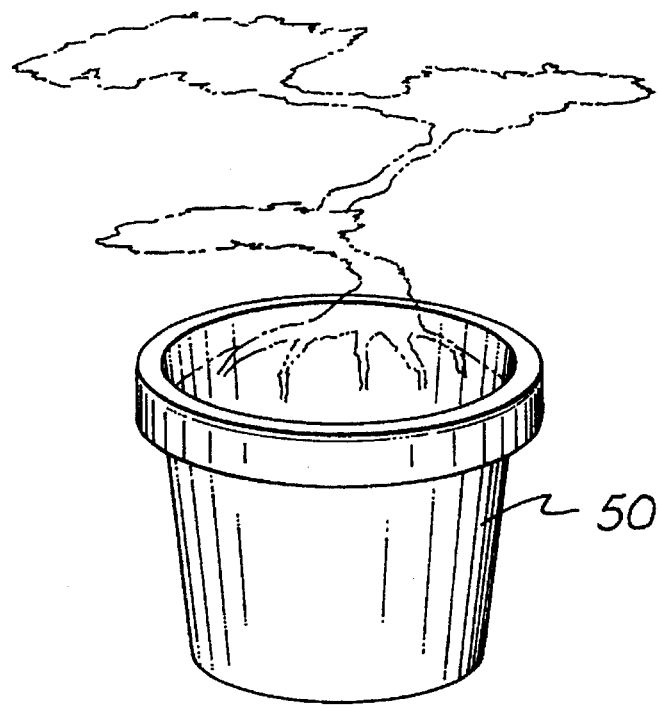
FIG. 5 is a perspective view of a pot for a plant in accordance with the present invention.
Figure 6:
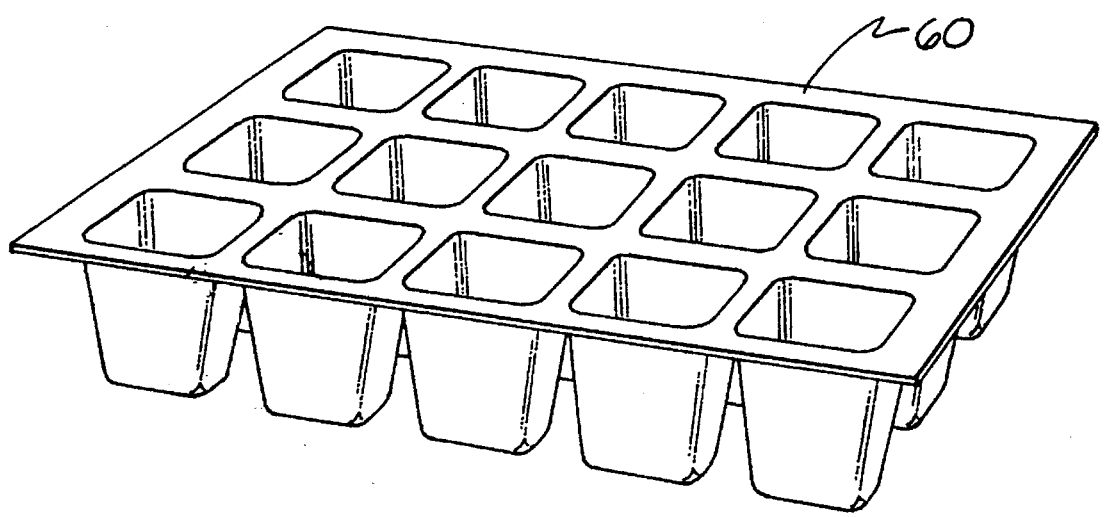
FIG. 6 is a tray for plants for germination of seeds made in accordance with the present invention.

FIGS. 5 and 6 represent further articles made from the composition of the present invention. Illustrated in the figures is a floral bucket 50 and a plant starter tray 60. The anti-microbial agents contained within the products protect the plants and seedlings from microbial attack. Further, the anti-microbial agents destroy or inhibit any harmful microorganisms found within the soil or any soil additives. Vitamin E controls the rate of release of the anti-microbial agents so that active concentrations do not harm or retard the growth of the plants. Preferably, floral bucket 50 includes about 500 ppm OBPA, 2,500 ppm TBZ, and 1,000 ppm vitamin E. Plant starter tray 60 would preferably contain 250 ppm OBPA, 2,500 ppm TBZ, 1,000 ppm vitamin E. Of course, these amounts vary depending upon the type of plant grown. For instance, less OBPA be used for tomato plants due to their low resistance to arsenic.

The composition of the present invention can also be ground into particles and granules of any particular size. The particles or granules can be used in agricultural applications for protecting row crops or for golf course greens and grass. The vitamin E, added in appropriate amounts, controls the rate of release of the anti-microbial agents so as not to harm plants. Further, the vitamin E ensures biocidal activity for a substantial period of time. In one particular application, the granules include OBPA in an amount of approximately 500 ppm, TBZ in an amount of approximately 2,500 ppm, and vitamin E in an amount of approximately 1,000 ppm.

The present invention may be better understood by reference to the following examples.

EXAMPLE 1

A test was conducted to determine the rate of migration of anti-microbial agents from a polymeric film. Specifically, the film was constructed from a polyvinylcholoride and contained about 150 ppm of OBPA, 5,000 ppm of TBZ, and 1,000 ppm of vitamin E. One side of the film was exposed to a 50 percent alcohol solution and deionized water. The alcohol was a non-denatured ethanol. The ethanol/water solution was tested for arsenic after four days and then again after seven days. Arsenic tests were conducted using a graphite furnace following EPA Method 206.2. The following results were obtained:

|  | After 4 days | After 7 days |
| --- | --- | --- |
| Arsenic (ppb) | less than 5.0 | 6.0 |

When compared with biocide release rates as shown in Example 2 below, the results here indicate that the rate of migration was effectively controlled through the use of vitamin E. Such low levels of arsenic control growth of microorganisms and are also safe for human handling and contact with consumables.

EXAMPLE 2

Migration tests were also conducted on pieces of polyvinylchloride (PVC) and thermopolyurethane (TPU) tubing impregnated soley with OBPA (no vitamin E). The pieces of tubing were immersed in water for extended periods of time. The water was then tested for arsenic using a graphite furnace. The following results were obtained:

| Sample | Arsenic (ppb) concentration | | |
|---|---|---|---|
| | After 24 Hours | After 48 Hours | After 68 Hours |
| PVC with 307 ppm OBPA | 230 | 280 | 410 |
| TPU with 690 ppm OBPA | 1200 | 990 | 2800 |
| TPU with 730 ppm OBPA | 2800 | 1460 | 4540 |

The results illustrate much higher levels of arsenic than recorded in Example 1.

It should be understood that the present invention is not limited to the specific compositions or methods described herein and that any composition having a formula or method steps equivalent to those described falls within the scope of the present invention. Preparation routes of the composition and method steps for controlling the release of anti-microbial agents are merely exemplary so as to enable one of ordinary skill in the art to make the composition and use it according to the described process and its equivalents. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the following claims.

What is claimed is:

1. An anti-microbial additive for adding to polymeric materials consisting essentially of:

a biocide comprising an organically bound arsenic; and vitamin E in an amount effective to slow the rate of release of said biocide from a polymeric material when said anti-microbial additive has been added to said polymeric material.

2. The anti-microbial additive as defined in claim 1, wherein said organically bound arsenic is 10,10'-oxybisphenoxarsine.

3. The anti-microbial additive as defined in claim 2, wherein said organically bound arsenic is contained a liquid carrier of epoxidized soybean oil.

4. The anti-microbial additive as defined in claim 1, wherein said organically bound arsenic is 10,10'-oxbisphenoxarsine and is present in relation to said vitamin E in a ratio of about 1:1.

5. The anti-microbial additive as defined in claim 1, wherein said biocide further includes 2-(4'-thiazolyl)benzimidazole.

6. An anti-microbial additive for adding to polymeric materials consisting essentially of:

10,10'-oxybisphenoxarsine;

2-(4'-thiazolyl)benzimidazole; and vitamin E present in an amount effective to slow the rate of release of said 10,10'-oxybisphenoxarsine and said 2-(4'-thiazolyl)benzimidazole from a polymeric material when said anti-microbial additive has been incorporated into said polymeric material.

7. The anti-microbial additive as defined in claim 6, wherein said 10,10'-oxybisphenoxarsine is present in relation to said vitamin E in a ratio of about 1:1.

8. An aseptic polymeric material containing controlled release anti-microbial agents consisting essentially of:

a polymeric composition containing a biocide and vitamin E, said biocide and said vitamin E being dispersed within said polymeric composition, said vitamin E being present in said polymeric composition in an amount effective to slow the rate of release of said biocide from said composition.

9. The aseptic material as defined in claim 8, wherein said biocide comprises an organically bound arsenic and 2-(4'thiazolyl)benzimidazole.

10. The aseptic material as defined in claim 8, wherein said polymeric composition is selected from the group consisting of polyalkalenes, polyolefins, polyvinyls, synthetic rubbers, latex fibers, synthetic fibers, and mixtures thereof.

11. The aseptic material as defined in claim 9, wherein said organically bound arsenic is present in said material in an amount from about 5 ppm to about 2,000 ppm.

12. The aseptic material as defined in claim 8, wherein said vitamin E is present in said material in an amount from about 50 ppm to about 2,000 ppm.

13. An aseptic, polymeric material containing controlled release anti-microbial agents consisting essentially of:

2-(4'-thiazolyl)benzimidazole;

a polymeric composition having said 2-(4'-thiazolyl)benzimidazole dispersed within said composition; and vitamin E also dispersed within said polymeric composition.

14. The aseptic, polymeric material as defined in claim 13, wherein said aseptic material is selectively used to make films, sheets, or tubing.

15. The aseptic, polymeric material as defined in claim 13, wherein said polymeric material is selected from the group consisting of polyethylene, polypropylene, polystyrene, polyacrylate, polyvinylchloride, nylon, polyurethane, and mixtures thereof.

16. An aseptic polymeric article containing controlled release anti-microbial agents consisting essentially of:

a biocide for destroying and inhibiting the growth of microorganisms, wherein said biocide is a material selected from the group consisting of 10,10'-oxybisphenoxarsine, 2-(4'-thiazolyl)benzimidazole, and mixtures thereof;

a polymeric composition wherein said biocide is dispersed; and vitamin E dispersed within said polymeric composition in an amount sufficient to slow the rate of migration of said biocide from said polymeric composition.

17. The aseptic article as defined in claim 16, wherein said article is dental tubing.

18. The aseptic article as defined in claim 16, wherein said article is in granule form for protecting agricultural products from microbial attack and infestation.

19. The aseptic article as defined in claim 16, wherein said article is a container for protecting plants from attack and infestation by microorganisms.

20. A polymeric dental tube containing controlled release anti-microbial agents consisting essentially of:

an elongated hollow tube made from a polymeric material;

a biocide contained within said polymeric material, wherein said biocide is a material selected from the group consisting of 10,10'-oxybisphenoxarsine, 2-(4'-thiazolyl)benzimidazole, and mixtures thereof, said biocide for inhibiting the growth of microorganisms found within said dental tube; and vitamin E added in an amount sufficient to slow the rate of release of said biocide from said polymeric material.

21. The aseptic dental tube as defined in claim 21, wherein said biocide is made from a blend of 10,10'-oxybisphenoxarsine and 2-(4'-thiazolyl)benzimidazole, said 10,10'-oxybisphenoxarsine being present in said tube in an amount from about 50 ppm to about 500 ppm, said 2-(4'-thiazolyl)benzimidazole being present in an amount from about 1,000 ppm to about 3,000 ppm, and said vitamin E being present in an amount from about 500 ppm to about 1,500 ppm.

22. The aseptic, polymeric material as defined in claim 13, further consisting of 10,10'-oxybisphenoxarsine.

23. The aseptic, polymeric material as defined in claim 13, wherein said 2-(4'-thiazolyl)benzimidazole is present in said material in an amount from about 5 ppm to 5,000 ppm.

24. The aseptic, polymeric material as defined in claim 23, wherein said vitamin E is present in said material in an amount from about 50 ppm to 2,000 ppm.

25. The aseptic article as defined in claim 16, wherein said article is a plastic bag.

26. A method for controlling the release of anti-microbial agents from a polymeric material comprising the steps of:

providing a polymeric substrate having at least one surface;

dispersing within said polymeric substrate a biocide; and also dispersing within said polymeric substrate a chemical controller comprising vitamin E, said chemical controller being added to said polymeric substrate in an amount sufficient to slow the migration of said biocide to said at least one surface.

27. A method as defined in claim 26, wherein said biocide is a material selected from the group consisting of an organically bound arsenic, 2-(4'-thiazolyl)benzimidazole, and mixtures thereof.

28. A method as defined in claim 26, wherein said vitamin E is present within said polymeric substrate in an amount from 50 ppm to 2,000 ppm.

29. A method as defined in claim 26, further comprising the step of adding said biocide and said vitamin E to said polymeric substrate while said polymeric substrate is in a molten state.

30. A method as defined in claim 26, wherein said biocide and said vitamin E are first combined prior to being dispersed within said polymeric substrate.

31. A method as defined in claim 26, wherein said biocide comprises a mixture of 10,10'-oxybisphenoxarsine and 2-(4'-thiazolyl)benzimidazole.

32. A method for controlling the release of anti-microbial agents from a polymeric material comprising the steps of:

providing a polymeric substrate having at least one surface;

adding to said polymeric substrate a biocide, said biocide comprising a material selected from the group consisting of 10,10'-oxybisphenoxarsine, 2-(4'-thiazolyl)benzimidazole, and mixtures thereof, said biocide migrating from within said polymeric substrate to said at least one surface over a period of time; and adding vitamin E to said polymeric substrate in an amount sufficient to slow the rate of release of said biocide from said polymeric substrate.

33. A method as defined in claim 32, wherein said vitamin E is present within said polymeric substrate in an amount from about 50 ppm to 2,000 ppm.

34. A method as defined in claim 32, wherein said biocide comprises 2-(4'-thiazolyl)benzimidazole, said 2-(4'-thiazolyl)benzimidazole being present within said polymeric substrate in an amount from about 5 ppm to 5,000 ppm.

35. A method as defined in claim 32, wherein said biocide comprises a mixture of 2-(4'-thiazolyl)benzimidazole and 10,10'-oxybisphenoxarsine.

\* \* \* \* \*